United States Patent [19]
Izzo et al.

[11] Patent Number: 5,240,734
[45] Date of Patent: Aug. 31, 1993

[54] REDUCED-FAT PEANUT BUTTER COMPOSITIONS AND METHODS FOR PREPARING SAME

[75] Inventors: Henry J. Izzo, Bridgewater; Robert E. Lieberman, Morris Township, Morris County, both of N.J.

[73] Assignee: Healthy Foods Solutions, Morris Township, Morris County, N.J.

[21] Appl. No.: 708,484

[22] Filed: May 31, 1991

[51] Int. Cl.$^5$ ............................ A23L 1/38; A23J 3/08; A23J 3/14
[52] U.S. Cl. ................................... 426/633; 426/656; 426/657
[58] Field of Search ............... 426/633, 656, 657, 613, 426/585, 580, 582

[56] References Cited

U.S. PATENT DOCUMENTS 3,216,830 11/1965 Melnick ............................... 426/633
3,580,729  5/1971 Darragh et al. ..................... 426/633

Primary Examiner—Jeanette Hunter
Assistant Examiner—Helen Pratt
Attorney, Agent, or Firm—Richard R. Muccino

[57] ABSTRACT

A composition and method of making a reduced fat peanut butter in the form of a water-in-oil emulsion which contains a continuous peanut butter oil phase of peanut butter, and a protein complexing agent to maintain the consistency of the continuous peanut butter oil phase, and a discontinuous aqueous coagulated protein phase to reduce the fat content of the peanut butter which contains a coagulable dairy or vegetable protein and a protein coagulating agent.

20 Claims, No Drawings

REDUCED-FAT PEANUT BUTTER COMPOSITIONS AND METHODS FOR PREPARING SAME

BACKGROUND OF THE INVENTION

1. Field of the Invention

This invention pertains to reduced-fat peanut butter compositions. More particularly, this invention pertains to peanut butter compositions in the form of water-in-oil emulsions which comprise a continuous peanut butter oil phase and a discontinuous aqueous coagulated protein phase. The aqueous protein phase comprises an aqueous solution of a coagulable protein, a protein coagulating agent. The aqueous protein phase extends the peanut butter oil phase to provide peanut butter compositions having fewer calories and less fat than conventional peanut butter compositions. The improved peanut butter compositions may be used directly or may be incorporated into edible carriers to provide a wide variety of ingestible compositions.

2. Description of the Prior Art

Peanut butter is a cohesive, comminuted mixture of ground peanut particles suspended in liquid peanut oil. Peanut butter is prepared by roasting, blanching, and grinding shelled peanuts to form a peanut paste. During the grinding step, the cellular structure of the peanuts is ruptured releasing the peanut oil in which the pulverized peanut particles become suspended. A stabilizing agent such as a high melting point fat is generally added to the peanut paste to prevent separation of the phases. An emulsifying agent, a sweetening agent, and salt may also be added to the peanut paste.

The protein content of peanut butter is from about 26% to about 30% making peanut butter a nutritious food. The oil or fat content of peanut butter, however, is from about 48% to about 53% mitigating the nutritional value of peanut butter. Accordingly, low-fat peanut butters having the flavor and texture of conventional peanut butters are desirable.

Attempts to make low-fat peanut butter have generally focused on removing a portion of the peanut oil found in peanuts and replacing the oil with a low-fat and low-calorie filler substitute. These low-calorie peanut butter compositions have generally been unsatisfactory because the peanut oil removal step tends to also remove a portion of the flavor components from the peanut butter resulting in a peanut butter with poor taste. In addition, the low-fat filler substitutes generally do not provide the texture and consistency properties of conventional peanut butter.

U.S. Pat. No. 4,863,753, issued to Hunter et al., discloses a reduced-calorie peanut butter composition in which a portion of the peanut oil is replaced by triglycerides containing medium chain fatty acids.

U.S. Pat. No. 4,814,195, issued to Yokovama et al., discloses a reduced-calorie peanut butter composition containing from about 15% to about 40% of a low-calorie solid bulking agent such as polydextrose or microcrystalline cellulose.

U.S. Pat. No. 4,228,190, issued to Wallgren et al., discloses a margarine composition in the form of a water-in-oil emulsion which comprises a fat phase present in an amount from about 35% to about 65% and an aqueous precipitated protein phase, present in an amount from about 35% to about 65%. Wallgren et al. forms the aqueous precipitated protein phase by coagulating milk protein with rennet and the calcium already present in casein. Wallgren et al. does not teach to add a protein complexing agent.

U.S. Pat. No. 3,580,729, issued to Darragh et al., discloses a peanut spread supplemented with from about 15% to about 25% of soybean protein and from about 15% to about 25% of liquid vegetable oil.

U.S. Pat. No. 3,552,980, issued to Cooper et al., discloses a spreadable food product consisting of two discrete spreads in contact with each other. One spread is hydrophilic such as a peanut butter and the other spread is a modified sweet aqueous spread such as a jelly. The sweet aqueous spread is modified to contain in the non-aqueous portion less than 50% carbohydrates having a molecular weight of less than about 200 to prevent migration of moisture from the sweet aqueous spread to the hydrophilic spread.

U.S. Pat. No. 2,388,91, issued to Oatman, discloses a method for precipitating casein from dried skim milk which consists of mixing the dried skim milk with fresh skim milk and precipitating the casein with an acid, sour whey, or rennet.

While the above references disclose a variety of reduced-fat peanut butter compositions, none of the above compositions are entirely satisfactory. Removing peanut oil from peanut butter results in a peanut butter lacking flavor and adding low-fat filler substitutes results in a peanut butter with poor texture and consistency. Thus it would be commercially advantageous to provide a reduced-fat peanut butter composition which has the flavor and consistency of conventional peanut butter. The present invention provides such improved reduced-fat peanut butter compositions without the disadvantages characteristic of previously known products. This invention also pertains to methods for preparing these reduced-fat peanut butter compositions and the ingestible compositions in which they may be employed.

SUMMARY OF THE INVENTION

This invention pertains to a reduced-fat peanut butter composition in the form of a water-in-oil emulsion which comprises (A) a continuous peanut butter oil phase which comprises (a) peanut butter, and (b) an effective amount of a protein complexing agent to maintain the consistency of the continuous peanut butter oil phase, and (B) an effective amount of a discontinuous aqueous coagulated protein phase to reduce the fat content of the peanut butter which comprises (a) a coagulable protein selected from the group of dairy and vegetable proteins consisting of milk protein, egg protein, soy bean protein, and peanut protein, and (b) a protein coagulating agent.

DETAILED DESCRIPTION OF THE INVENTION

Applicants have discovered a reduced-fat peanut butter composition in the form of a water-in-oil emulsion which comprises a continuous peanut butter oil phase and a discontinuous aqueous coagulated protein phase. The coagulated protein phase comprises a mixture of a coagulable protein and a protein coagulating agent. The coagulated and phase acts as a nutritious extender to reduce the fat content of the peanut butter. Coagulating the protein in the discontinuous aqueous phase physically stabilizes the aqueous phase and maintains the consistency of conventional peanut butter. By carefully controlling the temperature and time of the protein coagulation and the concentration of the protein complexing agent, the peanut butter oil phase and the aqueous protein phase can be smoothly mixed without causing separation of the peanut oil and peanut particle phases. Because the continuous oil phase contains peanut butter in undiluted form, the taste and consistency of the reduced-fat peanut butter composition is substantially the same as that of conventional peanut butter flavor.

Applicants have further discovered that the protein complexing agent enhances mixing of the peanut butter oil phase and the aqueous protein phase and produces a smooth peanut butter consistency. Applicants have found that when the peanut butter oil phase and the aqueous protein phase are mixed without a protein complexing agent, the resulting mixture becomes dry and difficult to mix. Furthermore, the heat generated during the shearing necessary to blend the mixture causes the peanut butter to separate. When the peanut butter oil phase and the aqueous protein phase are mixed in the presence of a protein complexing agent, the resulting mixture becomes smooth and easy to mix and the consistency of the continuous peanut butter oil phase is maintained.

Applicants believe that the protein in the peanut butter oil phase is hygroscopic and tends to absorb water from the aqueous protein phase when mixed with the aqueous phase causing the resulting mixture to become dry and difficult to mix. When a protein complexing agent is present in the aqueous phase, the peanut protein appears to complex with the complexing agent causing a change in conformation of the protein which results in a decrease in hygroscopicity. This reduced hygroscopicity results in less absorption of water by the peanut protein and smoother mixing of the oil and water phases. The flavor and consistency of the reduced-fat peanut butter compositions of the present invention are substantially the same as that of conventional peanut butter.

Applicants define the terms "ingestible" and "edible" to include all materials and compositions which are used by or which perform a function in the body. These include materials and compositions which are adsorbed and those which are not absorbed as well as those which are digestible and non-digestible.

In accord with the present invention, the reduced-fat peanut butter composition is in the form of a water-in-oil emulsion which comprises a continuous peanut butter oil phase and a discontinuous aqueous coagulated protein phase. The peanut butter which may be employed in the continuous oil phase may be any peanut butter known in the art. In general, peanut butter comprises peanut paste, a stabilizing agent, and optionally an emulsifying agent, a sweetening agent, and salt. Normally, peanut butter comprises peanut paste in an amount from about 75% to about 99%, by weight of the peanut butter.

Peanut paste is obtained by roasting, blanching, and grinding raw peanuts by methods well known in the food arts. Peanut paste may be made from a variety of peanuts and is preferably prepared from a blend of Runner, Spanish, and Virginia peanuts. The peanuts may be ground in any conventional manner such as in a comminuter, an attrition mill, a disintegrator, a hammermill, or a colloid mill. The extent of grinding may be adjusted to prepare the desired type of peanut butter having a smooth, regular, or chunky texture. The resulting peanut paste is a mixture of peanut particles suspended in peanut oil.

A stabilizing agent is generally added to the peanut butter to stabilize the peanut butter against separation of the peanut oil and solid peanut components. The stabilizing agent is usually mixed with the peanut paste and heated to melt the stabilizing agent. The mixture is then cooled to solidify the stabilizing agent as a continuous or semicontinuous matrix to provide rigidity to and prevent phase separation of the peanut butter mixture. Stabilizing agents are well known in the art and include partially and completely hydrogenated vegetable oils, monoglycerides and diglycerides of vegetable oils, and mixtures of these. Non-limiting examples of stabilizing agents include partially and completely hydrogenated natural fats such as peanut oil, corn oil, cotton seed oil, linseed oil, palm oil, rapeseed oil having an iodine value not greater than about 10, whale oil, and other marine oils, and the like, and mixtures thereof. The stabilizing agent is generally present in the peanut butter in an amount from about 1% to about 5%, preferably from about 1.5% to about 3%, and more preferably from about 1.5% to about 2.5%, by weight of the peanut butter oil phase.

An emulsifying agent may optionally be present in the peanut butter to aid in dispersing the immiscible components into a single stable system and to reduce stickiness so that the peanut butter will not adhere to the roof of the mouth. Non-limiting examples of emulsifying agents include glyceryl monostearate, lecithin, fatty acid monoglycerides, fatty acid diglycerides, propylene glycol monostearate, and the like, and mixtures thereof. A preferred emulsifying agent is glyceryl monostearate. The emulsifying agent may be employed in amounts from about 0.5% to about 1.5%, preferably from about 0.75% to about 1.25%, and more preferably from about 0.8% to about 1%, by Weight of the peanut butter oil phase.

A sweetening agent may optionally be present in the peanut butter. Non-limiting examples of sweetening agents may be selected from the group consisting of sucrose, dextrose, fructose, honey, molasses, aspartame, saccharin, and the like, and mixtures thereof. The sweetening agent will be present in the peanut butter in an amount from about 1% to about 10%, preferably from about 1% to about 5%, and more preferably from about 1% to about 3%, by weight of the peanut butter oil phase.

The peanut butter may also optionally contain salt as a flavoring agent in an amount from about 1% to about 1.5%, by weight of the peanut butter oil phase.

In general, the peanut butter in the peanut butter oil phase is prepared by admixing peanut paste, the stabilizing agent, and optional peanut butter ingredients to provide a uniform mixture. The mixture is usually heated and then cooled to recrystallize the stabilizing agent as a matrix to prevent phase separation of the peanut butter mixture. Preferably, the peanut butter is prepared under an inert atmosphere such as a nitrogen atmosphere.

The discontinuous aqueous coagulated protein phase comprises (a) an aqueous solution of a coagulable protein selected from the group of dairy and vegetable proteins consisting of milk protein, egg protein, soy bean protein, and peanut protein, (b) a protein coagulating agent, and (c) an effective amount of a protein complexing agent to maintain the consistency of the continuous peanut butter oil phase.

The coagulable protein in the discontinuous aqueous phase may be any edible protein which may be coagulated. Coagulation is the solidification of a solution into a gelatinous mass or an alteration of a disperse phase or of a dissolved solid which causes the separation of the system into a liquid phase and an insoluble mass known as a clot or curd. Non-limiting coagulable proteins may be selected from the group of dairy and vegetable proteins consisting of milk protein, egg protein, soy bean protein, and peanut protein.

The term "milk protein" as used herein refers to proteins present or derived from milk. Milk proteins include proteins derived from whole milk, low-fat milk, non-fat milk, buttermilk, powdered milk, and the like. The main proteins found in milk are casein, present in an amount of about 80%, and whey proteins which are beta-lactoglobulin or lactalbumin, present in an amount of about 20%.

Casein is a white, tasteless, odorless, nontoxic amorphous solid present to the extent of about 3% in bovine milk. Casein is a mixture of related phosphoproteins which contains all of the common amino acids and is rich in the essential amino acids. Casein is obtained from milk by removing the cream and acidifying the skimmed milk to cause casein to precipitate. Casein is also precipitated by lactic acid during fermentation of skimmed milk in cheese manufacture. The major components of casein are designated as alpha-, beta, gamma, and K-caseins, in order of decreasing electrophoresis mobility at pH 7.

Whey is the supernatant fluid remaining after precipitation of casein. The principle protein of bovine whey is beta-lactoglobulin, also known as lactalbumin, which constitutes from about 50% to about 60% of the whey protein.

The term "egg protein" as used herein is used in its common meaning and refers to proteins present or derived from egg. Egg proteins include proteins derived from egg white, dried egg white, and the like. The main protein found in egg is ovalbumin (egg white).

The term "soy protein" as used herein is used in its common meaning and refers to proteins present or derived from soy bean, soy bean meal, and the like. The main protein found in soy bean is grain and soybean albumins.

The term "peanut protein" as used herein is used in its common meaning and refers to proteins present or derived from peanuts, peanut meats, peanut oil meal, and the like. Peanuts contain about 26% protein and peanut oil meal contains from about 39% to about 45% protein. The main proteins found in peanuts are the globulins arachin and conarachin.

The term "albumin" refers to a group of simple naturally occurring proteins characterized by heat coagubility and solubility in dilute solution. The most common albumins are lactalbumin (milk), ovalbumin (egg white), serum albumin (blood serum), and grain and soybean albumins. As set out above, the coagulable protein may be selected from the group of dairy and vegetable proteins consisting of milk protein, egg protein, soy bean protein, and peanut protein, preferably from the group of dairy protein consisting of milk protein and egg protein, and most preferably the coagulable protein is milk protein. The most preferred milk protein is casein.

The amount of coagulable protein present in the discontinuous aqueous phase of the present invention is an effective amount. An effective amount of coagulable protein is that amount of coagulable protein necessary to physically stabilize the aqueous phase and maintain the consistency of a conventional peanut butter. The exact amount of coagulable protein employed is subject to such factors as the type of coagulable protein employed in the mixture, the type of peanut butter oil phase employed, the other ingredients in the composition, and the type of final product desired. The exact amount of coagulable protein employed in the discontinuous aqueous phase may be varied in order to obtain the result desired in the final product and such variations are within the capabilities of those skilled in the art without the need for undue experimentation. In a preferred embodiment, the coagulable protein in the discontinuous aqueous phase will be present in an amount from about 1% to about 5%, preferably from about 1.5% to about 4.5%, and more preferably from about 2% to about 4%, by weight of the discontinuous aqueous phase.

The protein coagulating agent in the present invention is an agent such as a proteolytic enzyme, an acid, or sour whey which will coagulate or clot the coagulable proteins of the invention. Suitable protein coagulating acids include lactic acid, hydrochloric acid, and sulfuric acid. The amount of protein coagulating acid present in the discontinuous aqueous phase of the present invention is an amount effective to coagulate the protein. Such amounts of coagulating acid are well known in the art and are not the subject of the present invention. In a preferred embodiment, the protein coagulating agent is a protein coagulating enzyme.

The protein coagulating enzymes in the present invention are proteolytic enzymes which will coagulate or clot the coagulable proteins of the invention. The protein coagulating enzyme is an enzyme which does not continue its hydrolytic activity after curd formation. In general, such enzymes are catalyzed by calcium which is normally present in the coagulable protein. Suitable protein coagulating enzyme may be selected from the group consisting of rennin, *Mucor miehei, Mucor pusillus, Endothia parasitica,* porcine pepsin, and mixtures thereof. Other proteolytic enzymes can be used to coagulate proteins providing that their hydrolytic activity does not continue after curd formation. In a preferred embodiment, the protein coagulating enzyme is selected from the group consisting of rennin and Mucor miehei.

Rennin (chymosin, rennase) is an endopeptidase secreted by the stomach which causes the curdling of milk. Rennin is a single polypeptide chain with internal disulfide bridges and has the power to coagulate 25,000 times its weight of milk. Rennet is a commercially available dried extract containing rennin which is used in the manufacture of cheese, rennet casein, junket and rennet custards.

The amount of protein coagulating enzyme present in the discontinuous aqueous phase of the present invention is an effective amount. An effective amount of protein coagulating enzyme is that amount of enzyme necessary to coagulate the coagulable protein in a suitable period of time. In general, the protein coagulating enzyme should coagulate the protein just after mixing of the peanut butter oil phase and the aqueous protein phase is complete and before the discontinuous aqueous phase becomes unstable. The protein coagulating enzyme should not coagulate the protein before mixing of the peanut butter oil phase and the aqueous protein phase is complete. When the protein is coagulated before mixing of the phases is complete, mixing becomes difficult and the heat generated during mixing can cause the phases to separate. The exact amount of protein coagulating enzyme employed is subject to such factors as the type of protein coagulating enzyme employed in the mixture, the type of coagulable protein employed, the temperature at which the mixing of the peanut butter oil phase and the aqueous protein phase is conducted, the other ingredients in the composition, and the type of final product desired. The exact amount of protein coagulating enzyme employed in the discontinuous aqueous phase may be varied in order to obtain the result desired in the final product and such variations are within the capabilities of those skilled in the art without the need for undue experimentation. In a preferred embodiment, the protein coagulating enzyme in the discontinuous aqueous phase will be present in an amount from about 0.01% to about 1.2%, preferably from about 0.01% to about 0.08%, and more preferably from about 0.01% to about 0.06%, by weight of the discontinuous aqueous phase.

The protein complexing agent in the present invention is a compound which will complex with the peanut protein, reduce the hygroscopicity of the protein, enhance mixing of the peanut butter oil phase and the aqueous protein phase, and produce a smooth peanut butter consistency. Preferably, the protein complexing agent is a divalent metal ion selected from the group consisting of non-toxic water-soluble calcium compounds and magnesium compounds. More preferably, the protein complexing agent is a non-toxic water-soluble calcium compound which can also serve to catalyze the protein coagulating enzyme. Suitable non-limiting examples of calcium and magnesium compounds include calcium chloride, calcium carbonate, calcium sulfate, calcium lactate, calcium oxalate, calcium gluconate, calcium propionate, magnesium chloride, magnesium carbonate, magnesium sulfate, magnesium lactate, magnesium oxalate, magnesium gluconate, magnesium propionate, and the like, and mixtures thereof. In a preferred embodiment, the protein complexing agent is a calcium compound selected from the group consisting of calcium gluconate, calcium lactate, calcium propionate, and mixtures thereof. In a more preferred embodiment, the calcium compound is calcium gluconate.

The amount of protein complexing agent present in the discontinuous aqueous phase of the present invention is an effective amount. An effective amount of protein complexing agent is that amount of protein complexing agent necessary to enhance mixing of the peanut butter oil phase and the aqueous protein phase, maintain the consistency of the continuous peanut butter oil phase, produce a smooth peanut butter consistency, and catalyze the protein coagulating enzyme to coagulate the protein. The exact amount of protein complexing agent employed is subject to such factors as the type of protein complexing agent employed in the mixture, the protein coagulating enzyme employed, the coagulable protein employed, the other ingredients in the composition, and the type of final product desired. The exact amount of protein complexing agent employed in the discontinuous aqueous phase may be varied in order to obtain the result desired in the final product and such variations are within the capabilities of those skilled in the art without the need for undue experimentation. In a preferred embodiment, the protein complexing agent in the discontinuous aqueous phase will be present in an amount from about 0.1% to about 1.5%, preferably from about 0.2% to about 1.2%, and more preferably from about 0.3% to about 1%, by weight of the discontinuous aqueous phase.

The pH value of the aqueous phase is generally adjusted to optimize coagulation of the protein by the protein coagulating enzyme and to maximize the shelf stability of the reduced-fat peanut butter composition. In general, the pH of the discontinuous aqueous phase will be in the range from about 3.8 to about 6.5, preferably from about 4 to about 6, and more preferably from about 4.2 to about 5.8. The pH of the discontinuous aqueous phase can be adjusted by adding a pH adjusting or buffering agent such as sodium hexametaphosphate (sodium polymetaphosphate), citric acid, phosphoric acid, lactic acid, and mixtures thereof. The exact amount of pH adjusting or buffering agent necessary to obtain a particular pH value is well known and within the capabilities of those skilled in the art without the need for undue experimentation.

In another embodiment, the shelf stability of the reduced-fat peanut butter composition can be enhanced by incorporating water-soluble solids such as carbohydrates into the aqueous protein phase prior to admixing the aqueous protein phase with the peanut butter oil phase. Non-limiting examples of water-soluble solids include dextrose, sucrose, fructose, maltodextrins such as low DE (dextrose equivalence) maltodextrins, lactose, vegetable gums such as acacias, guar, karaya, and mixtures thereof. Preferred sources of water-soluble solids are sugar syrups and light corn syrup. Sufficient water-soluble solids should be incorporated into the aqueous protein phase to obtain a water activity in the range from about 0.65 to about 0.99, preferably from about 0.7 to about 0.85, and more preferably from about 0.75 to about 0.82. The soluble solids value will be in the range from about 55% to about 72%, preferably from about 60% to about 68%, by weight of the aqueous phase. The shelf stability of the reduced-fat peanut butter composition can also be improved by incorporating preservatives such as potassium sorbate and sodium benzoate into the composition and by pasteurizing the peanut butter composition.

In yet another embodiment, the texture and consistency of the reduced-fat peanut butter compositions can be enhanced by incorporating chelating agents into the aqueous high soluble solids phase prior to admixing the aqueous high soluble solids phase with the peanut butter oil phase. Peanut butter compositions which contain an aqueous high soluble solids phase tend to have a stringy texture because of the presence of metal ions. When a chelating agent is added to the aqueous high soluble solids phase, the chelating agent tends to chelate the metal ion, reduce the body of the aqueous composition, and prevent the formation of a stringy texture. Suitable chelating agents in the present invention include sodium hexametaphosphate, sodium acid pyrophosphate, sodium tripolyphosphate, sodium citrate, and the like, and mixtures thereof. In a preferred embodiment, the chelating agent is selected from the group consisting of sodium hexametaphosphate and sodium acid pyrophosphate, and mixtures thereof. In a more preferred embodiment, the chelating agent is sodium hexametaphosphate.

The amount of chelating agent present in the discontinuous aqueous phase of the present invention is an effective amount. An effective amount of chelating agent is that amount of chelating agent necessary to chelate metal ions, prevent stringy texture, and produce a smooth peanut butter consistency. The exact amount of chelating agent employed is subject to such factors as the type of chelating agent employed in the mixture, the type and amount of metal ions present in the composition, the other ingredients in the composition, and the type of final product desired. The exact amount of chelating agent employed in the discontinuous aqueous phase may be varied in order to obtain the result desired in the final product and such variations are within the capabilities of those skilled in the art without the need for undue experimentation. In a preferred embodiment, the chelating agent in the discontinuous aqueous phase will be present in an amount from about 0.01% to about 1.5%, preferably from about 0.02% to about 1%, and more preferably from about 0.03% to about 0.7%, by weight of the discontinuous aqueous phase.

The amount of discontinuous aqueous coagulated protein phase present in the continuous peanut butter oil phase of the present invention is an effective amount. An effective amount of discontinuous aqueous coagulated protein phase is a sufficient amount of discontinuous aqueous coagulated protein phase to reduce the fat or oil content of the peanut butter composition to a significant value without inverting the water-in-oil emulsion into an oil-in-water emulsion. The exact amount of discontinuous aqueous coagulated protein phase employed is subject to such factors as the type of discontinuous aqueous coagulated protein phase employed in the mixture, the type of peanut butter oil phase, the other ingredients in the composition, and the type of final product desired. The exact amount of discontinuous aqueous coagulated protein phase employed in the continuous peanut butter oil phase may be varied in order to obtain the result desired in the final product and such variations are within the capabilities of those skilled in the art without the need for undue experimentation. In a preferred embodiment, the discontinuous aqueous coagulated protein phase in the reduced-fat peanut butter composition will be present in an amount from about 10% to about 90%, preferably from about 10% to about 80%, and more preferably from about 10% to about 60%, by weight of the reduced-fat peanut butter composition.

The present invention extends to methods for making the reduced-fat peanut butter compositions. The peanut butter components are admixed using standard techniques and apparatus known to those skilled in the art. In a typical method, the reduced-fat peanut butter compositions of the present invention are prepared by admixing the continuous peanut butter oil phase and an effective amount of the discontinuous aqueous coagulated protein phase. Other ingredients will usually be incorporated into the composition as dictated by the nature of the desired composition as well known by those having ordinary skill in the art. The ultimate peanut butter compositions are readily prepared using methods generally known in the food technology and confectionery arts.

In a preferred embodiment, the components of the discontinuous aqueous coagulated protein phase are first premixed before admixing the discontinuous aqueous coagulated protein phase with the continuous peanut butter oil phase. Premixing the components of the discontinuous aqueous coagulated protein phase forms a more intimate mixture of components which reacts more efficiently in the enzymatic protein coagulation reaction. For example, the protein coagulating agent or enzyme can be dissolved in an aqueous solution of a coagulable protein and protein complexing agent at a temperature of about 38° C. to about 50° C. over a period of about 2 to 10 minutes. The optimal temperatures utilized may vary depending upon the type of coagulable protein, the protein coagulating agent or enzyme, and the protein complexing agent used, but such temperatures are readily determined by those skilled in the art without undue experimentation. Once the discontinuous aqueous coagulated protein phase is premixed, the aqueous phase is then dispersed throughout the continuous peanut butter oil phase by generating enough shear force with such mixing equipment as a Stephen Cutter, Waring Blender, Bowl Chopper, and the like, to form globules of about 50 microns or less to emulsify the aqueous phase in the oil phase. This emulsification step should preferably take place in a temperature controlled state so that the stabilizing agent does not liquify and cause the phases to separate. The protein coagulating enzyme generally reacts with the coagulable protein over a period of about 20 minutes to about 1 hour depending upon the temperature of the water-in-oil emulsion, generally from about 20° C. to about 50° C., to coagulate the protein and stabilize the aqueous phase so that the aqueous phase remains in the oil phase as discrete small particles.

In a specific embodiment, the present invention is directed to a method for preparing a reduced-fat peanut butter composition in the form of a water-in-oil emulsion which comprises the steps of:

(1) providing the following ingredients:

(A) a peanut butter oil phase which comprises:

(a) peanut butter; and (b) an effective amount of a protein complexing agent to maintain the consistency of the continuous peanut butter oil phase; and (B) an effective amount of an aqueous protein phase to reduce the fat content of the peanut butter which comprises:

(a) an aqueous solution of a coagulable protein selected from the group of dairy and vegetable proteins consisting of milk protein, egg protein, soy bean protein, and peanut protein;

(b) a protein coagulating agent; and (c) a protein complexing agent; and (2) admixing the peanut butter oil phase and the aqueous protein phase to form a reduced-fat peanut butter composition in the form of an water-in-oil emulsion having a continuous peanut butter oil phase and a discontinuous aqueous coagulated protein phase.

The peanut butter compositions may be prepared using standard techniques and equipment known to those skilled in the art. The apparatus useful in accordance with the present invention comprises mixing and heating apparatus well known in the food and confectionery manufacturing arts, and therefore the selection of the specific apparatus will be apparent to the artisan.

The reduced-fat peanut butter compositions of the present invention have improved taste and texture properties over conventional reduced-fat peanut butter compositions and fewer calories than conventional peanut butter compositions.

Once prepared, the reduced-fat peanut butter compositions may be used directly, may be stored for future use, or may be formulated in effective amounts with conventional edible carriers, in place of regular peanut butter, to prepare a wide variety of edible compositions such as cookies, candies, sauces, and the like. The preparation of edible and confectionery formulations is historically well known and has changed little through the years. The reduced-fat peanut butter compositions of the present invention can be incorporated into edible carriers by admixing the inventive peanut butter composition into conventional confections. A general discussion of the composition and preparation of confections may be found in B. W. Minifie, *Chocolate, Cocoa and Confectionery: Science and Technology*, 2nd edition, AVI Publishing Co., Inc., Westport, Conn. (1980), at pages 424–425, which disclosure is incorporated herein by reference.

The amount of the inventive reduced-fat peanut butter composition employed in an edible composition is an effective amount to provide satisfactory flavor and nutritional value to the edible composition. The exact amount of the reduced-fat peanut butter composition employed is a matter of preference, subject to such factors as the type of edible carrier employed in the composition, the type of reduced-fat peanut butter composition employed, and the other ingredients in the composition. Thus, the amount of reduced-fat peanut butter composition may be varied in order to obtain the result desired in the final product and such variations are within the capabilities of those skilled in the art without the need for undue experimentation. In general, the amount of reduced-fat, peanut butter composition normally present in an edible composition will be up to about 90%, preferably from about 20% to about 85%, and more preferably from about 25% to about 80%, by weight of the edible composition.

A variety of traditional ingredients may be optionally included in effective amounts in the edible composition. Such ingredients include antioxidants, preservatives, and the like. Suitable anti-oxidants include butylated hydroxytoluene (BHT), butylated hydroxyanisole (BHA), propyl gallate, and mixtures thereof. Suitable preservatives include potassium sorbate, sodium benzoate, calcium propionate, and mixtures thereof. Other conventional additives known to one having ordinary skill in the food and confectionery art may also be used in the edible composition.

The present invention extends to methods for making the ingestible compositions. In such a method, a composition is made by admixing an effective amount of the reduced-fat peanut butter composition of the present invention with an edible carrier and the other ingredients of the final desired ingestible composition. The reduced-fat peanut butter composition may be admixed with the edible carrier in any conventional manner such as by preparing a homogeneous mixture of the components, forming a peanut butter core coated by an edible carrier such as chocolate, or coating a confectionery carrier with the peanut butter composition. Other ingredients will usually be incorporated into the composition as dictated by the nature of the desired composition as well known by those having ordinary skill in the art. The ultimate ingestible compositions are readily prepared using methods and apparatus generally known in the food technology arts.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLES 1-2

These examples demonstrate the preparation of peanut butter compositions employing a discontinuous aqueous gelatin phase.

The aqueous gelatin compositions employed in the peanut butter compositions of Examples 1 and 2 had the compositions set out below.

| Aqueous Gelatin Compositions | | |
|---|---|---|
| | Examples | |
| Ingredients | 1 | 2 |
| Water | 50% | 51.5% |
| Sucrose | 47% | 47% |
| Gelatin | 3% | 1.5% |

The aqueous gelatin compositions of Examples 1 and 2 were admixed and heated to the boiling point of the compositions. The gelatin solutions were then cooled to about 44° C. and admixed with an equivalent amount by weight of peanut butter (Skippy) in a Waring Blender.

The peanut butter mixture of Example 1 quickly became viscous and difficult to blend. The heat generated during the shearing necessary to blend the mixture caused the peanut butter oil to separate. Oil separation was also observed in the peanut butter mixture of Example 2. After refrigeration, the peanut butter mixture of Example 2 was also judged unacceptable because the mixture had a jello-like texture.

EXAMPLE 3

This example demonstrates the preparation of a peanut butter composition employing a discontinuous aqueous light pancake syrup phase.

Light pancake syrup (Log Cabin) and peanut butter were admixed in equal amounts by weight in a Waring Blender. The peanut butter mixture was easy to blend well initially but soon became very viscous. The heat generated during the shearing necessary to blend the mixture caused the peanut butter oil to separate. Cooling the peanut butter, the light pancake syrup, or both before admixing the components did not prevent phase separation.

EXAMPLE 4

This example demonstrates the preparation of a reduced-fat peanut butter composition comprising a discontinuous aqueous coagulated protein phase, which is immobilized after being admixed into peanut butter, in accord with present invention.

The aqueous protein composition employed in the peanut butter composition of Example 4 had the composition set out below.

| Aqueous Protein Composition | |
|---|---|
| Ingredients | Example 4 |
| 1% Fat Milk | 16 oz |
| Aqueous Rennet solution (5%) | 10 g |
| Calcium Gluconate | 4 g |
| Sucrose | 34 g |
| Gelatin | 4 g |
| Aqueous Vanilla Solution (1%) | 3.5 g |

The components of the aqueous protein composition, except for the aqueous rennet solution, were admixed and heated to about 50° C. The aqueous rennet solution was then added to the protein mixture and the entire mixture was admixed with an equivalent amount by weight of peanut butter in a Waring Blender.

The peanut butter mixture of Example 4 was initially quite fluid and easy to blend. After about 20 to 25 seconds of being mixed, the peanut butter mixture began to thicken and smooth and finally set within a period of about 2 to about 4 minutes. The resulting peanut butter product had very good peanut butter taste, texture, color, and spreadability.

EXAMPLES 5-6

These examples demonstrate the preparation of peanut butter compositions employing a discontinuous soluble solids aqueous phase with and without a calcium compound.

The aqueous soluble solids compositions employed in the peanut butter compositions of Examples 5 and 6 had the compositions set out below.

| Soluble Solids Aqueous Compositions | | |
|---|---|---|
| | Examples | |
| Ingredients | 5 | 6 |
| Light Pancake Syrup | 50% | 49.05% |
| Sucrose solution (60%) | 50% | 49.05% |
| Calcium Gluconate | — | 1.9 g |

The aqueous soluble solids compositions of Examples 5 and 6 were admixed and heated to the boiling point of the compositions. The solutions were then cooled to about 44° C. and admixed with an equivalent amount by weight of peanut butter in a Waring Blender.

The peanut butter mixture of Example 5 soon became dry and stiff. The heat generated during the shearing necessary to blend the mixture caused the peanut butter to separate. The peanut butter mixture of Example 6 did not become dry and was easy to mix.

These Examples demonstrate that the protein in the peanut butter oil phase tends to absorb water from the aqueous high soluble solids phase causing the resulting two-phase mixture to become dry and difficult to mix. When a calcium compound is present in the aqueous phase, the peanut protein appears to complex with the calcium resulting in a decrease in hygroscopicity. This reduced hygroscopicity results in less absorption of water by the peanut protein and smoother mixing of the oil and water phases.

EXAMPLES 7-8

These examples demonstrate the preparation of reduced-fat peanut butter compositions employing a discontinuous soluble solids aqueous phase with and without a chelating agent.

The aqueous soluble solids compositions with and without the chelating agent sodium hexametaphosphate employed in the peanut butter compositions of Examples 7 and 8 had the compositions set out below.

| Soluble Solids Aqueous Compositions | | |
|---|---|---|
| | Examples | |
| Ingredients | 7 | 8 |
| Light Corn Syrup | 49.6% | 50% |
| Aqueous Protein Phase from Example 4 | 49.6% | 50% |
| Sodium hexameta-Phosphate | 0.05% | — |
| Salt | 0.03% | |

The aqueous soluble solids compositions of Examples 7 and 8 were admixed and heated to the boiling point of the compositions. The solutions were then cooled to about 44° C. and admixed with an equivalent amount of peanut butter by weight peanut butter in a Waring Blender.

The peanut butter mixture of Example 8 had a stringy type texture. The peanut butter mixture of Example 7 had very good texture and spreadability. These Examples demonstrate that when a chelating agent is added to the aqueous high soluble solids phase, the chelating agent tends to reduce the body of the aqueous composition and prevent the formation of a stringy texture.

EXAMPLES 9-12

These examples demonstrate the preparation of shelf-stable reduced-fat peanut butter compositions employing a discontinuous aqueous coagulated protein phase in accord with present invention.

The shelf-stable reduced-fat peanut butter compositions of Examples 9-12 were prepared by reducing the water activity and the pH value of the compositions to levels sufficient to render the products shelf stable. The compositions of the shelf-stable peanut butters of Examples 9-12 are set out below.

| Reduced-Fat Peanut Butter Compositions | | | | |
|---|---|---|---|---|
| | Examples | | | |
| Ingredients | 9 | 10 | 11 | 12 |
| Peanut butter | 40% | 50% | 50% | 50% |
| Aqueous Protein Phase from Example 4 | 20% | 12.5% | 12.5% | 12.5% |
| Light Corn Syrup from Example 7 | 20% | 30% | 30% | 30% |
| Low DE maltodextrin | 20% | 7.5% | 7.5% | 7.5% |
| Water Activity | 0.89 | 0.82 | 0.82 | 0.82 |
| pH | 5.9 | 5.9 | 5.7 | 5.72 |

The peanut butter composition of Example 9 had a water activity of 0.89 and a pH value of 5.9 which were considered not sufficiently low for shelf stability. The peanut butter composition of Example 10 had a water activity of 0.82 and a pH value of 5.9 which were considered satisfactory values for shelf stability. The peanut butter composition of Example 10 had a strong peanut butter taste, was fortified with calcium, and had half the fat of normal peanut butter. The peanut butter composition of Example 11, which was the same composition as that in Example 10 except that the pH value of the light corn syrup was lowered, had a slightly acidic tangy taste. The peanut butter composition of Example 12, which was the same composition as that in Example 10 except that the pH value of the light corn syrup was lowered, had very little tangy taste and was considered as having satisfactory shelf stability.

The embodiments of the present invention described herein are merely exemplary and are not intended to limit the scope of the invention. Many variations and modifications may be made without departing from the spirit and scope of the invention. Applicants intend that all such modifications and variations are to be included within the scope of the invention as defined in the appended claims and their equivalents.

We claim:

1. A reduced-fat peanut butter composition in the form of a water-in-oil emulsion which comprises:
   (A) a continuous peanut butter oil phase which comprises:

(a) peanut butter; and (b) an effective amount of a protein complexing agent to maintain the consistency of the continuous peanut butter oil phase; and (B) a discontinuous aqueous coagulated protein phase to reduce the fat content of the peanut butter present in the reduced-fat peanut butter composition in an amount from about 10% to about 90% by weight, which comprises:

(a) a coagulable dairy and vegetable protein selected from the group consisting of milk protein, egg protein, soy bean protein, and peanut protein present in the discontinuous aqueous coagulated protein phase in an amount from about 1% to about 5% by weight; and (b) a protein coagulating agent.

2. The peanut butter composition according to claim 1, wherein the discontinuous aqueous coagulated protein phase is a premixed phase.

3. The peanut butter composition according to claim 1, wherein the coagulable protein is milk protein.

4. The peanut butter composition according to claim 1, wherein the protein coagulating agent is a protein coagulating enzyme selected from the group consisting of rennin, *Mucor miehei, Mucor pusillus, Endothia parasitica*, porcine pepsin, and mixtures thereof.

5. The peanut butter composition according to claim 1, wherein the protein complexing agent is selectable from the group consisting of non-toxic water-soluble calcium compounds and magnesium compounds.

6. The peanut butter composition according to claim 5, wherein the protein coagulating enzyme is present in the discontinuous aqueous coagulated protein phase in an amount from about 0.01% to about 1.2%, by weight of the discontinuous aqueous coagulated protein phase.

7. The peanut butter composition according to claim 1, wherein the protein complexing agent is present in the continuous peanut butter oil phase in an amount from about 0.1% to about 1.5%, by weight of the continuous peanut butter oil phase.

8. The peanut butter composition according to claim 1, wherein the discontinuous aqueous coagulated protein phase further comprises sufficient water-soluble solids to yield a water activity in the range from about 0.65 to about 0.99 and a water-soluble solids value from about 55% to about 72% by weight of the discontinuous aqueous coagulated protein phase.

9. The peanut butter composition according to claim 1, wherein the discontinuous aqueous coagulated protein phase further comprises a chelating agent present in an amount from about 0.01% to about 1.5%, by weight of the discontinuous aqueous coagulated protein phase.

10. An edible composition which comprises an edible carrier and a reduced-fat peanut butter composition in the form of a water-in-oil emulsion, wherein the peanut butter composition comprises:

(A) a continuous peanut butter oil phase which comprises:

(a) peanut butter: and (b) an effective amount of a protein complexing agent to maintain the consistency of the continuous peanut butter oil phase; and (B) a discontinuous aqueous coagulated protein phase to reduce the fat content of the peanut butter present in the reduced-fat peanut butter composition in an amount from about 10% to about 90%, by weight, which comprises:

(a) a coagulable dairy and vegetable protein selected from the group consisting of milk protein, egg protein, soy bean protein, and peanut protein present in the discontinuous aqueous coagulated protein phase in an amount from about 1% to about 5%, by weight; and (b) a protein coagulating agent.

11. The edible composition according to claim 10, wherein the discontinuous aqueous coagulated protein phase is a premixed phase.

12. The edible composition according to claim 10, wherein the coagulable protein is milk protein 13. The edible composition according to claim 10, wherein the protein coagulating agent is a protein coagulating enzyme selected from the group consisting of rennin, *Mucor miehei, Mucor pusillus, Endothia parasitica*, porcine pepsin, and mixtures thereof.

14. The edible composition according to claim 10, wherein the protein complexing agent is selected from the group consisting of non-toxic water-soluble calcium compounds and magnesium compounds.

15. The edible composition according to claim 10, wherein the reduced-fat peanut butter composition is present in the edible composition in an amount up to about 90%, by weight of the edible composition.

16. A method for preparing reduced-fat peanut butter composition in the form of a water-in-oil emulsion which comprises the steps of:

(1) providing the following ingredients:

(A) a continuous peanut butter oil phase which comprises peanut butter; and (B) a discontinuous aqueous coagulated protein phase to reduce the fat content of the peanut butter present in the reduced-fat peanut butter composition in an amount from about 10% to about 90%, by weight, which comprises:

(a) a coagulable dairy and vegetable selected from the group proteins consisting of milk protein, egg protein, soy bean protein, and peanut protein present in the discontinuous aqueous coagulated protein phase in an amount from about 1% to about 5%, by weight;

(b) a protein coagulated agent; and (c) an effective amount of a protein complexing agent to maintain the consistency of the continuous peanut butter oil phase;

(2) admixing the peanut butter oil phase and the aqueous protein phase to form a reduced-fat peanut butter composition in the form of an water-in-oil emulsion having a continuous peanut butter oil phase and a discontinuous aqueous coagulated protein phase.

17. The method according to claim 16, wherein the aqueous protein phase from step (1)(B) is premixed before step (2).

18. A reduced-fat peanut butter composition in the form of a water-in-oil emulsion prepared by a method which comprises the steps of:

(1) providing the following ingredients:

(A) a continuous peanut butter oil phase which comprises peanut butter; and (B) a discontinuous aqueous coagulated protein phase to reduce the fat content of the peanut butter present in the reduced-fat peanut butter composition in an amount from about 10% to about 90%, by weight, which comprises:

(a) a coagulable dairy and vegetable protein selected from the group consisting of milk protein, egg protein, soy bean protein, and peanut protein present in the discontinuous aqueous coagulated protein phase in an amount from about 1% to about 5%, by weight:

(b) a protein coagulated agent; and (c) an effective amount of a protein complexing agent to maintain the consistency of the continuous peanut butter oil phase;

(2) admixing the peanut butter oil phase and the aqueous protein phase to form a reduced-fat peanut butter composition in the form of an water-in-oil emulsion having a continuous peanut butter oil phase and a discontinuous aqueous coagulated protein phase.

19. The reduced-fat peanut butter composition according to claim 18, wherein the aqueous protein phase from step (1)(B) is premixed before step (2).

20. A peanut butter composition in the form of a water-in-oil emulsion which comprises:

(A) a continuous peanut butter oil phase which comprises:

(a) peanut butter; and (b) an effective amount of a protein complexing agent to maintaining the consistency of the continuous peanut butter oil phase; and (B) a discontinuous aqueous phase present in the peanut butter composition in an amount from about 10% to about 90%, by weight, which comprises an effective amount of water-soluble solids to yield a water activity in the range from about 0.65 to about 0.99 and a water-soluble solids value from about 55% to about 72%, by weight of the discontinuous aqueous phase.

* * * * *